(12) United States Patent
Berger et al.

(10) Patent No.: US 11,849,999 B2
(45) Date of Patent: Dec. 26, 2023

(54) COMPUTER-IMPLEMENTED METHOD FOR DETERMINING A POSITION OF A CENTER OF ROTATION OF AN EYE USING A MOBILE DEVICE, MOBILE DEVICE AND COMPUTER PROGRAM

(71) Applicant: Carl Zeiss Vision International GmbH, Aalen (DE)

(72) Inventors: Mario Berger, Milda (DE); Steffen Urban, Jena (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/153,641

(22) Filed: Jan. 12, 2023

(65) Prior Publication Data
US 2023/0157539 A1    May 25, 2023

Related U.S. Application Data

(63) Continuation of application No. PCT/EP2021/078905, filed on Oct. 19, 2021.

(30) Foreign Application Priority Data

Oct. 19, 2020   (EP) .................................... 20202529

(51) Int. Cl.
*A61B 3/113*   (2006.01)
*A61B 3/10*    (2006.01)
(Continued)

(52) U.S. Cl.
CPC ............... *A61B 3/113* (2013.01); *A61B 3/111* (2013.01)

(58) Field of Classification Search
CPC .......... A61B 3/113; A61B 3/02; A61B 3/102; A61B 3/1025; A61B 3/0075;
(Continued)

(56) References Cited

U.S. PATENT DOCUMENTS 6,692,127 B2    2/2004  Abitbol et al.
10,433,724 B2   10/2019 Kratzer et al.
(Continued)

FOREIGN PATENT DOCUMENTS

EP    1837699 A1      9/2007
WO    2010097161 A1   9/2010

OTHER PUBLICATIONS

Jung et al., "Camera trajectory estimation using inertial sensor measurements and structure from motion results," in Proceedings of the IEEE Computer Society, Conference on Computer Vision and Pattern Recognition, vol. 2, pp. I-732-II-737, Dec. 2001.
(Continued)

*Primary Examiner* — Dawayne Pinkney
(74) *Attorney, Agent, or Firm* — Tautz & Schuhmacher LLC; Georg M. Hasselmann (57) ABSTRACT

Computer implemented methods for mobile device, mobile devices and computer programs are utilized for determining the center of rotation of the eye. An image of an eye of a person is captured in at least two positions of the mobile device, and the position of the center of rotation is determined based on the images and the position. In a similar manner, optionally a pupil position may be determined.

16 Claims, 5 Drawing Sheets (51) Int. Cl.
  *A61B 3/12* (2006.01)
  *A61B 3/024* (2006.01)
  *A61B 3/02* (2006.01)
  *A61B 3/11* (2006.01)
(58) Field of Classification Search
  CPC ..... A61B 3/1015; A61B 3/1225; A61B 3/024;
                          A61B 3/032; A61B 3/005
  USPC ............... 351/209, 200, 205, 206, 208, 210,
                          351/221–223, 237, 239, 240, 245–246
  See application file for complete search history.

(56) References Cited

U.S. PATENT DOCUMENTS

| | | | |
|---|---|---|---|
| 2013/0235331 | A1 | 9/2013 | Heinrich et al. |
| 2016/0363995 | A1* | 12/2016 | Rougeaux ............... G06F 3/013 |
| 2017/0090220 | A1* | 3/2017 | Bonnin ................. A61B 3/113 |
| 2017/0322430 | A1 | 11/2017 | Fayolle et al. |
| 2018/0095295 | A1 | 4/2018 | Chene et al. |
| 2019/0222830 | A1* | 7/2019 | Edwin ................. G06F 3/04815 |
| 2019/0243448 | A1 | 8/2019 | Miller et al. |
| 2020/0104589 | A1 | 4/2020 | Sengelaub et al. |

OTHER PUBLICATIONS

Nützi et al., "Fusion of IMO and Vision for Absolute Scale Estimation in Monocular SLAM," Journal of Intelligent & Robotic Systems, vol. 61, pp. 287-299, Nov. 2010.

Kar et al., "A Review and Analysis of Eye-Gaze Estimation Systems, Algorithms and Performance Evaluation Methods in Consumer Platforms," IEEE Access, vol. 5, p. 16495-16519, Aug. 2017.

Perkins et al., "Simple method of determining the axial length of the eye," British Journal of Ophthalmology, vol. 60, No. 4, pp. 266 to 270, Apr. 1976.

Sachs, "Sensor Fusion on Android Devices: A Revolution in Motion Processing," Google Tech Talk available at https://www.youtube.com/watch?v=C7JQ7Rpwn2k&feature=youtu.be), uploaded Aug. 2, 2010, 20 sample screen shots submitted, last accessed Jan. 11, 2023.

Industrial Norm "Robots and robotic devices—Vocabulary", Mar. 2012,DIN EN ISO 8373:2012.

Industrial Norm "Ophthalmic optics—Spectacle lenses—Vocabulary (ISO 13666:2012)," German and English version EN ISO 13666:2012, Oct. 2013.

Wikipedia entry "M-Estimator," available at https://en.wikipedia.org/wiki/M-estimator, last edited Nov. 18, 2022, last accessed Jan. 11, 2023.

Wikipedia entry "Random Sample Consensus," available at https://en.wikipedia.org/wiki/Random_sample_consensus, last edited Jan. 10, 2023, last accessed Jan. 11, 2023.

Wikipedia entry "Triangulation," available at https://en.wikipedia.org/wiki/M-estimator, last edited Jul. 18, 2022, last accessed Jan. 11, 2023.

Extended European Search report of EP 20 202 529.2, which is a counterpart hereof, dated Mar. 31, 2021.

International Search Report and Written Opinion issued in PCT/EP2021/078905, from which this application claims priority, dated Jan. 19, 2022.

International Preliminary Report on Patentability issued in PCT/EP2021/078905, from which this application claims priority, dated Sep. 29, 2022.

Office Action by the Chinese Patent Office (CNIPA) issued in CN 202180049696.5, which is a counterpart hereof, dated May 31, 2023, and English translation thereof.

Industrial Norm "Begriffe der physiologischen Optik [Terms of physiological optics] (DIN 5340:1998)," DIN 5340:1998, Apr. 1998. Relevance is found at least in paragraph [0008] of the specification.

* cited by examiner

COMPUTER-IMPLEMENTED METHOD FOR DETERMINING A POSITION OF A CENTER OF ROTATION OF AN EYE USING A MOBILE DEVICE, MOBILE DEVICE AND COMPUTER PROGRAM

CROSS REFERENCE TO RELATED APPLICATIONS

This application is a continuation application of international application PCT/EP2021/078905, filed Oct. 19, 2021, which claims priority to European patent application EP 20 202 529.2, filed on Oct. 19, 2020, both of which are hereby incorporated by reference in their entireties.

TECHNICAL FIELD

The present application relates to computer-implemented methods for determining a position of a center of rotation of an eye using a mobile device, corresponding mobile devices as well as computer programs for such mobile devices.

BACKGROUND

A mobile device is a device which at least comprises a programmable processor, a display and a camera as well as further sensors like acceleration sensors or depth sensors, and which is to be designed to be carried by a person. That means that regarding dimensions and weight it is designed accordingly to be carriable. Typical examples for such mobile devices are smartphones or tablets, which nowadays in practically all available models include a touchscreen, one or more cameras, an acceleration and gyroscope sensor, sometimes other sensors like depth sensors and further components like wireless interfaces for mobile communication networks or wireless local area networks (WLAN). The weight of such mobile devices typically is at least below 2 kg, normally below 1 kg or significantly below that. Computer programs for such mobile devices usually are referred to as "apps" (short for applications).

For fitting spectacles (referred to as glasses in the following) to a person, nowadays various computer-implemented approaches are used. For example, U.S. Pat. No. 6,692,127 B2 describes a fitting system for glasses. In the course of such fitting, so-called centration parameters have to be determined. Some of these centration parameters are for example defined in chapter 5 of standard DIN EN ISO 13666:2012 and include for example the interpupillary distance (PD) according to item 5.29 of this standard. These centration parameters are nowadays often determined automatically via systems including cameras like the ZEISS VISUFIT 1000 system. Other centration parameters include the distance between the lenses of the glasses and the cornea of the eye.

For conventional glasses, these centration parameters are sufficient to adapt the glasses to a particular person. However, in recent years glasses have been developed which may provide additional information in the field of view of a person, so-called augmented reality (AR) glasses. An example for such AR glasses is described in US 2013/0 235 331 A1. For optimizing such AR glasses for a user and reducing complexity of the optical design, additional parameters are necessary compared to conventional glasses. In particular, the optical center of rotation of the eye which is the base point of the perpendicular drawn from the mechanical center of rotation to a fixation line (extended into the interior of the eye) when looking straight on to a point at infinity is required. The mechanical center of rotation is the point in the eye which, when the eye rotates, moves the least (in a perfect rotation of a sphere, this would be the center of the sphere). The mechanical center of rotation is defined in DIN 5340:1998-04 under item 42. The optical center of rotation is defined under item 43 as the intersection of the perpendicular drawn from the mechanical center of rotation to a line of sight when looking straight ahead extended into the interior of the eye with this line of sight.

Various methods for determining the position of the center of rotation of the eye are known from WO 2010/097 161 A1. In one of the methods disclosed therein, a calibrated camera system is used to determine axes which intersects in the center of rotation for two viewing directions of the eye. For this approach, a corresponding calibrated camera system is needed, which is for example provided in commercial centration devices. In addition, here, the target is fixed as it is not carriable, while the test person changes the viewing direction. Therefore, for this approach, corresponding commercial equipment is needed, which is usually available at an optician or doctor.

A further method for determining the position of the center of rotation is known from E. S. Perkins et al, "Simple method of determining the axial length of the eye", Br. J. Ophthalmol. Vol. 60, 266, 1976. This method uses a special camera system with two flashes to obtain cornea reflexes for different viewing directions. Also here, specific equipment with flash targets is necessary for determining the center of rotation of the eye and the camera, and viewing targets should be fixed at a certain position.

With this device, it is also possible to determine the axial length of the eye, also referred to as eye diameter. Determining the eye diameter is also known from EP 1 837 699 A1, there for determining parameters for progressive ophthalmic lenses. Also in this document, specific equipment is used.

Besides applications for glasses or lens design, the eye diameter may also be used for diagnostic purposes. For example, a change in the eye diameter over time, at least once every 6 months, typically at least once a year, may indicate possible myopia. Devices like the Oculus Myopia Master inter alia measure the axial length of the eye to determine possible myopia. Also here, a comparatively costly device is necessary which is provided usually only at opticians.

US 2019/243 448 A1 discloses a head mounted display (HMD) using an eye tracking camera to determine the center of rotation of an eye or both eyes of a person. In this approach, a specific HMD is required. A somewhat similar approach is disclosed in US 2017/322 430 A1, where a device for determining the center of rotation is fixedly mounted to a spectacle frame.

Therefore, it would be desirable to measure the center of rotation of an eye by simpler means, such that persons can also perform the measurement at home. Further, it would be desirable to be able to also measure the eye diameter by such simple means.

SUMMARY

In this regard, it is an object of the present disclosure to enable such measurements by utilizing the already-available mobile devices with low cost and increased convenience without the need of any additional and special equipment required in the related art.

This object is achieved by a method in which a person looks into a first and second direction while respectively capturing first and second images of the eye of the person, a mobile device for performing the method, and a corresponding computer program for the mobile device. Exemplary embodiments are discussed in detail below.

With such methods, mobile devices, and computer programs, measurement of the center of rotation of the eye or, in additional exemplary embodiments, also of the eye diameter, becomes possible with mobile devices like smartphones or tablets, which many people possess, in contrast to the specific equipment necessary for the related art discussed above. For example, by loading a computer program on such a device, the measurements discussed herein can be performed.

According to a first aspect of the disclosure, a method for determining the position of the center of rotation of an eye of a person in an arbitrary world coordinate system using a mobile device is provided, comprising:

capturing a first image of an eye portion of a person looking at a camera of the mobile device or a target displayed on a display of the mobile device with a camera of the mobile device in a first position in the arbitrary world coordinate system, moving, by the person or another person the mobile device to a second position relative to the head of the person, capturing a second image of the eye portion of the person looking at the camera of the mobile device or a target displayed on a display of the mobile device in the second position in the arbitrary world coordinate system, and determining the position of the center of rotation based on the first image, the second image, the first position of the mobile device and the second position of the mobile device.

In this way, a built-in camera of the mobile device may be used for determining the position of the center of rotation. As practically all mobile devices like smartphones or tablets has a camera, in this way hardware provided in the mobile device may be used, and no additional devices are required. Similar to the related art in WO 2010/097 161 A1 described above, first and second images are taken with different viewing directions of the person (towards the mobile device in the present disclosure, towards flash targets in the related art). However, unlike the related art, no calibrated camera system is needed, but a conventional device is used which is moved from the first position to the second position. Further, the calibrated camera system is fixed at a single position, whereas the mobile device of the present disclosure changes its position during the measurement.

"The person looking at the mobile device" means that the person looks at the mobile device in the first position when the first image is captured (corresponding to the person looking in a first direction), i.e., at the camera of the mobile device or the displayed target, and at the mobile device in the second position when the second image is captured (corresponding to the person looking in a second direction). It is assumed that the person holds his/her head upright when looking at the mobile device, for example at the camera. Furthermore, when determining the position of the center of rotation of an eye, the person keeps the head itself in a fixed position during the method, such that only the eyes move to look at the mobile device, in the first and second positions when the mobile device captures the first and second images, respectively. That is, the person changes the viewing direction following the mobile device, while not moving the head.

The eye portion is a part of the person including at least one eye, or both eyes. It may also cover more parts of the person (face, head etc.). The method may be performed for one eye, but also may be performed for two eyes simultaneously, by selecting the eye portion to cover both eyes.

The center of rotation of the eye, as used herein, refers to the optical center of rotation unless noted otherwise.

The mobile device displays or outputs via a loudspeaker corresponding instructions such as a visual cue to the person, i.e., to keep the head in the same position while "tracking" the mobile device, for example a camera thereof, with his or her eyes. In some exemplary embodiments, the mobile device may display an instruction to constantly maintain the distance between the person (target) and the camera (for example, to maintain a constant arm length) while capturing the images. Instead of the camera, also a target may be displayed on a display like a touchscreen of the mobile device adjacent to the camera. By issuing instructions, the method can be easily be performed by a person and enhances the accuracy of the measurement. It should be noted that moving the mobile device to the first and second positions may be performed by the person under examination (the images are kind of "selfies") or by any other person.

While the above method uses a first position and a second position, this is not to be construed to mean that no further positions may be used. In fact, in exemplary embodiments besides the first position and the second position, at least three positions, such as a third position, fourth position, etc. may be used. Using more positions with a correspondingly higher number of images (i.e., third image, fourth image, etc.) may increase the accuracy of the measurement, as usual when taking a higher plurality of measurements, through statistics (for example averaging between the measurements etc.). On the other hand, using more positions may extend the measurement time.

The first position and second position are positions in an arbitrary coordinate system, referred to as "arbitrary world coordinate system" herein, which is a mechanism to associate physical values to positions within a dataset. For example, in some exemplary embodiments, the first position may be used as the origin of such a world coordinate system. The first position and the second position are determined by sensors of the mobile device. For example, mobile devices usually include acceleration sensors, which is a device that measure acceleration caused by movement, vibration, collision, etc., and the first position may be taken as the origin of the world coordinate system, and the second position (and possibly further positions like third position, fourth position, etc.) may be determined by integrating the acceleration measured by the acceleration sensors.

The term "integrating" here refers to a double (mathematical) integration over time. Integrating the acceleration over time once gives the velocity, apart from an offset. Assuming that the mobile device does not move in the first position, this offset may be set to zero. Integrating the velocity over time again (resulting in a double integration over time) results in the position, plus an offset. Setting the offset to zero corresponds to setting the origin of the world coordinate system to the first position, as mentioned above.

In other exemplary embodiments, the mobile device may include an additional camera spaced apart from the camera, and the first and second positions may be obtained by stereometry using the camera and the additional camera. In some exemplary embodiments, at least one mobile device can be used depending on the number of measuring positions. For instance, when two measurements are made, two mobile devices may be set in two different positions or predetermined positions and used to capture the two images of an eye. In other exemplary embodiments, the mobile device may include a time of flight (TOF) camera or other depth sensor which measures the distance from objects in the field of view of the depth sensor, and the first and second positions may be determined using the depth sensor. In yet other exemplary embodiments, the mobile device may be configured for stereo projection. All these approaches have been implemented in commercially available smartphones or tablets, for example under the trademark iPhone TrueDepth for a projecting stereo system.

In yet other exemplary embodiments, further possibilities for determining position and orientation, i.e., the pose, of the mobile device may be used, for example as described in S.-H. Jung and C. Taylor, "Camera trajectory estimation using inertial sensor measurements and structure from motion results", in Proceedings of the IEEE Computer Society, Conference on Computer Vision and Pattern Recognition, vol. 2, 2001, pp. II-732-II-737" and Gabriel Nützi, Stephan Weiss, Davide Scaramuzza, Roland Stiegwart, "Fusion of IMO and Vision for Absolute Scale Estimation in Monocular SLAM, doi.org/10.1007/s10846-010-9490-z" described. Also techniques from sensor fusion as described in the tech talk entitled "Sensor Fusion on Android Devices: A Revolution in Motion Processing (InvenSense, available at the link in www.youtube.com/watch?v=C7JQ7Rpwn2k&feature=youtu.be)" may be used.

In some exemplary embodiments, the position of the center of rotation is additionally determined based on an orientation of the mobile device at the first position and second position (and possibly further positions). The orientation essentially indicates a rotational relationship between coordinate axes of a device coordinate system fixed to the mobile device to coordinate axes of the world coordinate system. The combination of position and orientation is also referred to as pose, as defined for example in DIN EN ISO 8373:2012. The orientation may be measured by an orientation sensor (also referred to as inclination sensor) of the mobile device, which is present in most available smartphones or tablets. Therefore, also in this case existing hardware may be used. Determining the orientation makes it easier for a person to carry out the method, as no special orientation needs to be kept. In other exemplary embodiments, the mobile device may be kept e.g. upright during the complete method, such that the orientation remains in a defined way.

Furthermore, the position of the center of rotation of the eye in exemplary embodiments may be determined based on angular characteristics of the camera. The angular characteristics indicate a relationship between an angle under which an object (in this case pupils of the eye) is relative to the optical axis of the camera and a picture element (pixel) of the image where the object appears. For a given camera with given camera optics, this relationship is fixed, and may be provided for example by a manufacturer (for example, a main parameter is the focal length of an objective lens of the camera together with dimensions and resolution of an image sensor of the camera, both of which parameters are provided by a manufacturer) or obtained by calibration.

The method may further comprise identifying pupil and/or the center of pupil of the eye in the first image and the second image. The term "pupil" is a hole located in the center of the iris of the eye that allows light to strike the retina. "The pupil center" or "the center of pupil of the eye" indicates the point of intersection of the maximum distances in the horizontal and vertical directions. Its movement represents the corresponding eye movement. The term "pupil (pupil center) of the person" indicates the pupil (pupil center) of the person (i.e., the user whose eyes are being measured) in the real world. Based on the pupil center identified in the first and second images taken while the person keeps his/her head in a fixed position with his/her eye following the mobile device moving from the first position to second position, respectively the position of the center of rotation can be determined. In this case, the pupil or pupil center in the phrase "identified pupil or pupil center in the first (second) image" or "pupil or pupil center identified in the first (second) image" is assumed to be in the first (second) position of the mobile device.

For the identification of the pupil or pupil center, any conventional approaches for pupil tracking may be used. For example, it can be tracked with classical image processing operations or with a learned model. An overview is given in A. Kar, P. Corcoran, "A Review and Analysis of Eye-Gaze Estimation Systems, Algorithms and Performance Evaluation Methods in Consumer Platforms", IEEE Access Vol. 5, DOI: 10.1109/ACCESS.2017.2735633. In other exemplary embodiments, machine learning methods may be used to analyze the images and determine the pupil or pupil center. For example, a neural network may be trained by images (first and second images, first and second further images) taking for calibration purposes, and the pupils may be manually annotated in these images to provide training data. Then, after training, the neural network may identify the pupil or pupil center.

To determine the center of rotation, any conventional triangulation methods can be used. For example, the triangulation methods as described in the online Wikipedia article available at en.wikipedia.org/wiki/Triangulation (computer vision) may be used. In this case, a line from the mobile device to the pupil looking at the first position and a line from the mobile device to the pupil looking at the second position may be determined. Typically, a line from the pupil identified in the first image captured by and displayed on the mobile device in the first position to the pupil of the person when looking at the mobile device in the first position and a line from the pupil identified in the second image captured by and displayed on the mobile device in the second position to the pupil of the person when looking at the mobile device in the second position may be determined. More typically, the pupils used to draw the lines may be the pupil center. In other words, two lines from the pupil center identified in the first and second images captured by and displayed on the mobile device in the first and second positions to the pupil center of the person when looking at the mobile device in the first and second positions (in particular the position of the camera or target the person looks at), respectively, may be determined. By using the pupil centers as the starting point of the lines other than mobile device and/or pupil itself, the measurement becomes more accurate and precise. With the identified pupil and/or pupil center in the image as described above, such a triangulation can be easily done by unprojecting a 2D point to 3D plane. If more than two positions and images are used, the corresponding number of lines may be drawn. Subsequently, the center of rotation may be estimated to be at an intersection of the first and second lines. In case of more than two positions, as the center of rotation as mentioned above is not a fixed point, various intersections close to each other may be determined, and the center of rotation may for example be taken as an average position of these intersections. Also, depending on measurement accuracy, the lines may not intersect precisely. To remove wrong or inaccurate pupil measurements from the input data, robust methods like random sample consensus (RANSAC) as described in the online Wikipedia article available at en.wikipedia.org/wiki/Random_sample_consensus or M-Estimators as described in the online Wikipedia article available at en.wikipedia.org/wiki/M-estimator as of Aug. 7, 2020 can be used here. As described above, in some exemplary embodiments, an instruction such as a visual cue including a guideline to assist the person to make accurate measurement (for example ordering not to move the head, to keep looking straight ahead, etc.), to repeat the measurement in a case where the measurements were not accurately made, etc. can be displayed on the display.

The above-mentioned methods have as a result the position of the center of rotation in the world coordinate system. The center of rotation is obtained in a 3D form. For some applications, the center of rotation relative to other features of the person are required, to be used later for various applications.

The center of rotation of the eye may be used for manufacturing lenses and glasses, in particular for AR glasses as mentioned initially. Therefore, the method for determining the center of rotation of the eye according to the present disclosure as described above may be used for manufacturing AR glasses. Generally, AR glasses are manufactured to cover the wide range of the center of rotation of the eye calibrated and determined based on available center of rotation data of any and every possible user. This was due to the difficulties in measuring center of rotation for each individual user. The present method enables easy and simple measurement of the center of rotation of an individual user and reduces the previous design effort required for manufacturing the AR glasses to cover all technical eye parameters of any and every possible user, as not center of rotation of any and every possible user have to be taken into account. By using the method of the present disclosure, the AR glasses may be easily tailored individually. For example, the eye box may be tailored to the person based on the center of rotation of the eye measured by the present method and needs not to be designed large enough to cover all persons, such that a smaller eye box may be used for the design. Therefore, the present method can be used for manufacturing AR glasses with a low cost and high efficiency.

In some exemplary embodiments, besides the position of the center of rotation of the eye in the world coordinate system, one or more additional landmark points of the person are determined in the world coordinate system by triangulation. For example, the position of the tip of the nose, the position of the corners of the eye, the position of the chin tip etc. may be determined and then provided together with the position of the center of rotation of the eye as reference points.

In other exemplary embodiments, the pupil position is determined and used as a reference point. For determining the pupil position, essentially the same methods as explained above for determining the center of rotation of the eye may be used, including details and variations discussed above, with the exception that in the first position and the second position (which may be the same as or different from the first and second positions for determining the center of rotation) the person keeps looking straight ahead in the rostral direction without moving the eyes (without changing the viewing direction), when the first and second images are taken in the first and second positions of the mobile device. Therefore, the positions of the mobile device for determining the pupil position may also be referred to as a further first position and a further second position, and the corresponding images as a further first image and a further second image, with the understanding that also in this case more than two further images and more than two further positions may be used.

Again, the person may be instructed by the instruction displayed on the mobile device to look accordingly. When determining the pupil position, the head position is maintained in the same position during the measurement as when determining the center of rotation of the eye. It should be noted that this determination of the pupil position may also be performed prior to determining the position of the center of rotation of the eye.

The method may further comprise identifying the pupil or pupil center in the further first image and the further second image. Here, the method and terms as described above will be used. Based on the pupil or pupil center identified in the further first and further second images taken while the person keeps his/her head in a fixed upright position and continues to look straight ahead (i.e., without changing the viewing direction), the pupil position can be determined. In this regard, the pupil center may be identified according to the method for identifying the pupil center described above used for the method for determining the center of rotation. Based on the identified pupil center, the pupil position then can be determined from the pupil center according to the method described above as to the method for determining the center of rotation. As a result, the pupil position is obtained in a 3D form.

The position of the center of rotation of the eye may then be given in relation to the pupil position. The pupil position is determined and used also in conventional centration parameter determination and adapting of lenses and glasses to a person, such that the information about the pupil position becomes available in this conventional process and the position of the center of rotation of the eye may be referenced to it.

In other exemplary embodiments, the position of the pupil and the position of the center of rotation of the eye may be used to estimate a measure of an eye diameter of the eye.

A measure for the eye diameter is a quantity which indicates the size of the eye. The measure may also be given as an estimate of the eye radius, i.e., half the diameter. In a simple approach, the eye radius is estimated as the metric distance between the pupil position and the position of the center of rotation of the eye, and the eye diameter may be estimated as twice said radius. In this way, the measure for the eye diameter may be easily determined. In other exemplary embodiments, corrections may be applied to account for the difference between mechanical center of rotation and optical center of rotation. Based on the measured eye diameter, a focal length of a lens can be obtained. Subsequently, based on the obtained the focal length, eye power or strength can be calculated accordingly.

In some exemplary embodiments, the measure of the eye parameter may then be used for monitoring eye conditions. For example, the above method for estimating the measure of the eye diameter may be performed at regular or irregular intervals, and the results may be stored. Strong changes may indicate a clinical condition like increasing myopia, and the mobile device may then prompt the person to visit a doctor.

According to another aspect, a corresponding mobile device is provided. The mobile device comprises a camera, a processor and a storage for storing programs ("apps" as mentioned above) therein. By such a program, the mobile device is configured to perform any of the methods above, for example to capture a first image of an eye portion of a person at a first position of the mobile device, capture a second image of the eye portion at a second position of the mobile device, while the person keeps his or her head in the same position and looks at the mobile device at the first and second positions, respectively, and to determine the position of the center of rotation of an eye of the person based on the first image, the second image, the first position and the second position of the mobile device as discussed above.

The mobile device may also include sensors to determine the first and second positions and may also comprise a sensor like an orientation sensor to determine an orientation of the mobile device in the first position and the second position, as also explained above. Such sensors like inertial measurement units, acceleration sensors, gyroscope sensors, etc. are provided in commercially available mobile devices like smartphones and tablets in many cases, such that by corresponding programming such a conventional mobile device may be "converted" to a mobile device according to the second aspect, without needing a corresponding hardware. As already mentioned, the mobile device issues corresponding instructions to the person.

Corresponding computer programs are also provided. In this respect, it is to be understood that of course the mobile device cannot force the person to keep the head in the correct position and look at the mobile device or straight ahead as appropriate, such that the mobile device being configured accordingly and the computer program being designed accordingly means that the calculations are made based on the assumption that the person behaves accordingly.

BRIEF DESCRIPTION OF THE DRAWINGS

The disclosure will now be described with reference to the drawings wherein.

DESCRIPTION OF EXEMPLARY EMBODIMENTS

The exemplary embodiments described in the following use a mobile device like a smartphone or a tablet for determining the position of the center of rotation of the eye. Further, the exemplary embodiments may also use a mobile device for additionally determining the pupil position and then estimating a diameter of the eye, as explained above.

Figure 1:
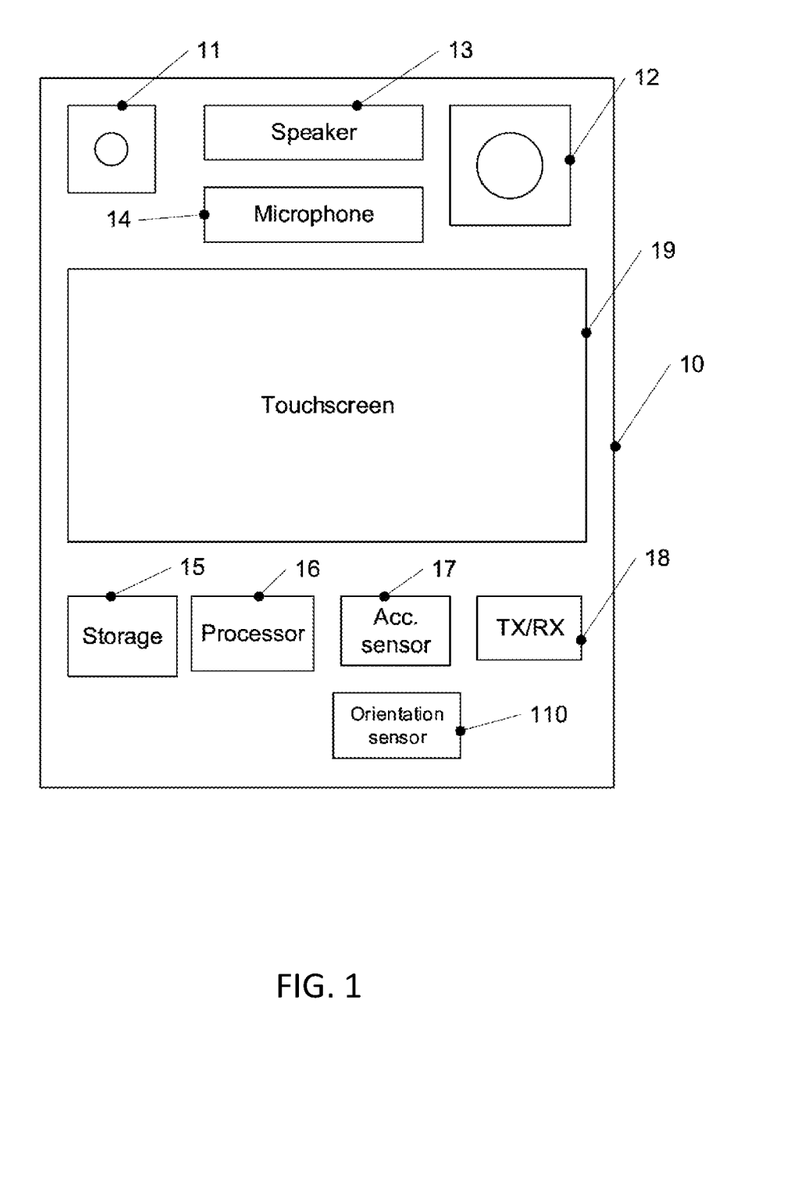
FIG. 1 shows a block diagram of a mobile device according to an exemplary embodiment.

FIG. 1 shows a block diagram of a mobile device 10 which is adapted by programming to be a mobile device according to the present disclosure. Smartphones or tablets nowadays available typically include at least the components shown in FIG. 1, but may also include further components.

Mobile device 10 of FIG. 1 includes a touchscreen 19, which is used as an input device as well as for outputting data, for example instructions to a person for performing the methods discussed above and discussed below with reference to FIG. 2. Mobile device 10 is controlled by a processor 16 which may access storage 15 (for example cloud, flash storage, random access memory, RAM, storage, read only memory, ROM, storage, memory cards inserted in the mobile device 10 etc.). Storage 15 may be used for storing computer programs, which as mentioned initially for mobile devices are also referred to as apps. In the case of FIG. 1, in storage 15 a computer program is stored to enable mobile device 10 to perform the methods discussed above or discussed below with respect to FIG. 2.

Mobile device 10 further includes a loudspeaker 13 for outputting sounds (speech, tones etc.) and a microphone 14. Via loudspeaker 13 mobile device 10 may also give instructions to the person performing the methods using sounds (in addition or as an alternative to outputting instructions on touchscreen 19), and microphone 14 may for example be used to receive spoken commands from the person.

Furthermore, mobile device 10 includes an acceleration sensor 17 for measuring accelerations of mobile device 10 and an orientation sensor 110 which may be used for measuring an orientation of mobile device 10. Such an orientation sensor 110 sometimes also is referred to as inclination sensor or gyroscope. While acceleration sensor 17 and orientation sensor 110 in FIG. 1 are shown as separate components, the functions may also be provided by a common sensor device.

Furthermore, a communication circuit for transmitting (TX) and receiving (RX) of data is provided, for example via a mobile communication network or a wireless local area network (WLAN). Via this communication circuit the determined parameters like position of the center of rotation of the eye or eye diameter may be provided to further entities, for example to an optician, a doctor or a manufacturer of glasses or lenses like augmented reality (AR glasses) and may then be used there subsequently.

Mobile device 10 further comprises a front camera 11 and a back camera 12. Front camera 11 is provided at the same side of mobile device 10 as touchscreen 19, such that using front camera 11 an eye portion of a person viewing touchscreen 19 may be captured. Back camera 12 is provided at the opposite side of touchscreen 19. Either front camera 11 or back camera 12, or both of them may be used in methods discussed herein.

Figure 2:
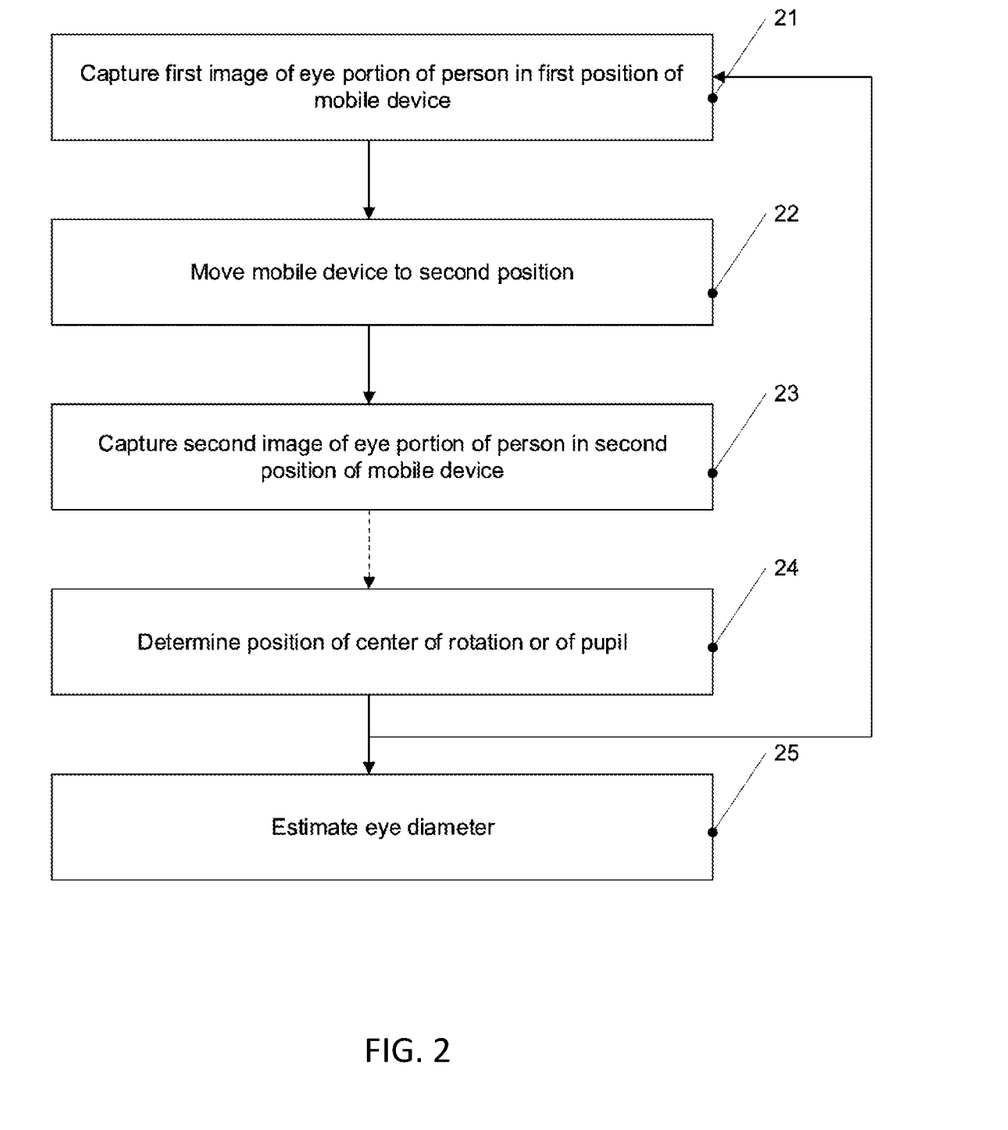
FIG. 2 shows a flowchart illustrating a method according to an exemplary embodiment.

FIG. 2 illustrates a method according to an exemplary embodiment which may be implemented by programming mobile device 10 and processor 16 thereof accordingly, by providing a corresponding computer program in storage 15. The method of FIG. 2 will additionally be explained referring to FIGS. 3 to 6.

At 21, the method comprises capturing a first image of an eye portion of a person in a first position of the mobile device.

At 22, the method comprises moving the mobile device to a second position. In exemplary embodiments using acceleration sensor 17 of the mobile device, the acceleration is integrated during the movement, such that the second position may be determined.

At 23, the method comprises capturing a second image of the eye portion of the person in the second position of the mobile device. As indicated by a dashed arrow between steps 23 and 24, the steps at 22 and 23 may be repeated for further positions like third position, fourth position etc., before the method moves on to step 24.

At step 24, the method comprises determining the position of a center of rotation of an eye of the person or the position of a pupil of the person based on the first image, the second image, the first position and the second position of the mobile device. For determining the center of rotation, the person, during execution of the method, keeps his or her head in the same position, but looks at the mobile device at the first position at 21 and looks at the mobile device at the second position at 23. For determining the position of the pupil, the person keeps the head in the same position and continues to look straight ahead without changing the viewing direction while the mobile device being moved. The steps 22 to 24, as indicated by an arrow, may be performed twice, once for determining the position of the center of rotation and once for determining the position of the pupil. The order is arbitrary, i.e., first the position of the center of rotation and then the position of the pupil may be determined, or vice versa.

Figure 3:
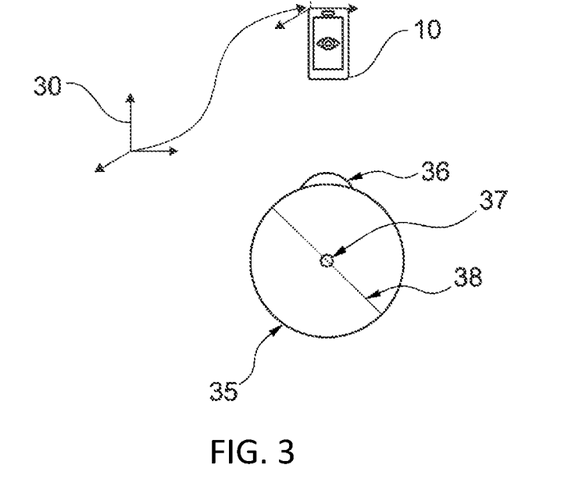
FIG. 3 shows an eye to be measured.

The steps 21 to 24 will now be illustrated further referring to FIGS. 3 to 6.

t is a diagram explaining the measurement situation in steps 21 to 24. An eye to be measured is shown as including a vitreous body 35 and a pupil 36. Furthermore, the mechanical center of rotation 37 and an eye diameter 38 are indicated.

Mobile device 10 in steps 21 to 24 is provided at least at a first position and a second position. The positions are given in a world coordinate system 30. World coordinate system 30 may have an arbitrary origin and arbitrary axis orientations. Furthermore, in FIG. 3 a device coordinate system 31 fixed to mobile device 10 is shown. For example, in cuboid-like mobile devices like a smartphone or a tablet, the axis directions may coincide with the directions of the edges of cuboid, as shown in FIG. 3. In some exemplary embodiments, for example device coordinate system 31 in the first position may be used as world coordinate system, such that the first position is at coordinates (0,0,0).

Mobile device 10 has a program installed thereon to perform the method. The program includes a pupil tracker, i.e., software components which enable the identification of pupil 36 and/or pupil center in images of the eye.

The orientation of mobile device 10 may be given as angle between device coordinate system 31 and world coordinate system 30, such that in the above example in the first position the angle is 0, and then depend on how much mobile device 10 is tilted with respect to the world coordinate system. The origin of the world coordinate system 31 may be set to a position of a camera of the mobile device, such that position and orientation of mobile device 10 gives position and orientation of the eye camera of mobile device 10 used. Mobile device 10 includes for example back camera 12 or front camera 11, depending on which camera is used for capturing the first and second images.

$T_w^C = [R_w^C, t_w^C]$, Generally, in the calculations below position and orientation of the mobile device is taken as position and orientation of the camera of mobile device 10 used. As mentioned, position and orientation together are also referred to as pose and may be written as vector $T_w^C = [R_w^C, t_w^C]$, where T is the pose, $_w$ indicates that it is the pose in the world coordinate system and $^C$ indicates that it refers to the camera, R is the orientation vector (given for example as three angles describing rotation of device coordinate system 31 with respect to world coordinate system 30), and t is a translation vector describing the position of the origin of device coordinate system 31 with respect to world coordinate system 30.

Figure 4:
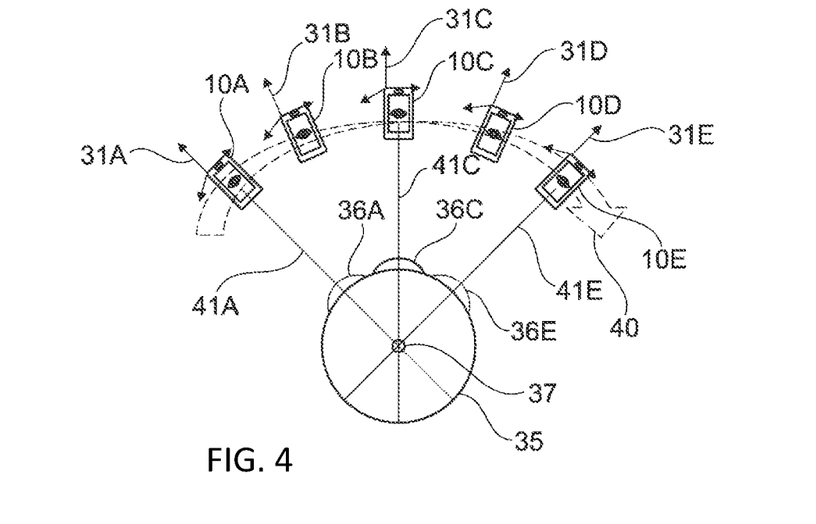
FIG. 4 shows the determination of the center of rotation of an eye.

FIG. 4 illustrates the method of FIG. 2 for determining the position of the center of rotation. In this case, the head of the person is to remain in the same fixed position, while looking towards mobile device 10, typically at the camera thereof.

In FIG. 4, as an example five positions of mobile device 10 are shown, where the mobile device at the five positions is denoted 10A, 10B, 10C, 10D, and 10E, respectively. The corresponding device coordinate systems 31 are denoted 31A, 31B, 31C, 31D, and 31E, respectively. The mobile device 10 may for example be moved from position to position along an arrow 40. The five positions as shown are examples for the first position, second position and three more positions in the method of FIG. 2.

The position of pupil 36 when the person looks at the mobile device, for example at the camera thereof, is shown for three positions as an example. Pupil 36A corresponds to the position when the person looks at mobile device 10A, pupil 36C corresponds the position when looking at mobile device 10C, and pupil 36E corresponds to the position when looking at mobile device 10E. For mobile devices 10B and 10D, the position of pupil 36 is not explicitly shown for clarity reasons.

In each case, an image of the eye portion including the pupil 36 and/or pupil center is captured. Based on this image, the respective position of the mobile device and the respective orientation of the mobile device, a line from the mobile device (typically pupil, more typically pupil center) to the pupil (typically pupil center) of the person may be calculated in the world coordinate system 30. As an example, three lines 41A, 41C and 41E are shown in FIG. 4. Typically, these lines have substantially identical or identical length for more precise measurement. These lines intersect in the center of rotation 37 for an ideal rotation. Hence, the position of the center of rotation 37 may be determined. It should be noted that in real measurements, as already mentioned initially, the lines may not intersect precisely. In this case, an average position may be formed based on intersection points of different lines or points where lines are closest to each other.

The position of mobile devices 10A to 10E may be determined for example by integration of the acceleration, or by other sensors of mobile device 10 as explained above, like a stereo camera system, depth camera etc. The orientation is determined by inclination sensor 20. From this, therefore, the pose of the camera of mobile device 10 is known.

Furthermore, for a given angle of an object with respect to the optical axis, this object is captured at a particular portion of an image sensor of the camera. This is illustrated in FIG. 6.

Figure 6:
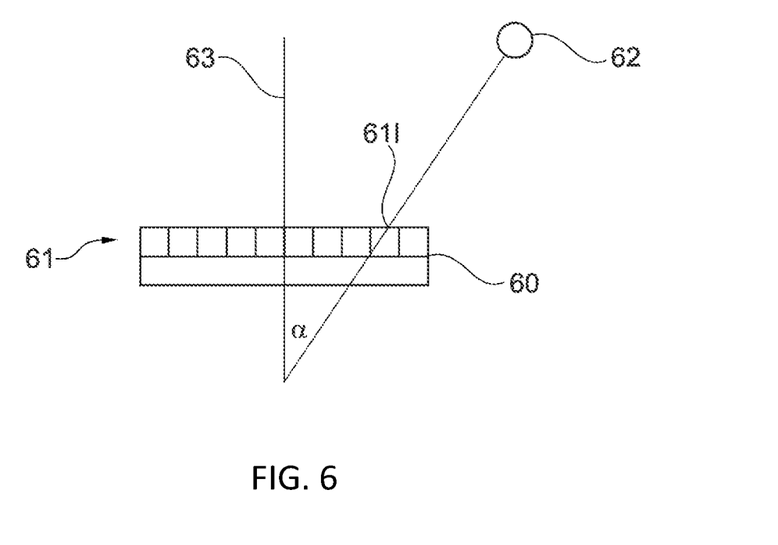
FIG. 6 shows an image sensor of a camera.

FIG. 6 shows an example image sensor 60 of camera 11 or 12, which includes a plurality of pixels 61, in a cross-sectional view. For illustration purposes ten pixels 61 are shown, which from left to right are designated 61A to 61I at the following. Resolutions of typical cameras of mobile devices are in the range of several megapixels, such that the representation of FIG. 6 is simplified for illustrations purposes.

An object 62, in case of FIG. 4 the pupil of an eye, which from the camera appears at an angle α to an optical axis 63 of the image sensor is imaged to a particular region of the image sensor, in the example of FIG. 6 to pixel 61I. This is true in two dimensions, i.e., also in a direction perpendicular to the cross-sectional view of FIG. 6. The relationship between angle α and pixel(s) to which an object like object 62 is imaged is fixed for a given camera and depends on the resolution and dimension of the image sensor and the properties, in particular focal length, of optics of the camera. The relationship therefore may be for example provided by a manufacturer of mobile device 10 or may be obtained by calibration, by arranging several test objects under several angles to the optical axis 63 of the camera.

Therefore, by capturing an image of the pupil and identifying on which region (i.e., which pixels) of the image sensor the pupil has been captured, a direction (angle α) relative to the optical axis 63 of the camera may be determined. The position of optical axis 63 follows immediately from the pose of the mobile device when capturing the image. Therefore, the respective lines 41A, 41C, and 41E of FIG. 4 may be determined, and hence the position of the center of rotation 37 may be determined.

For further use, the position of the center of rotation of the eye may then be given relative to the pupil center and may be transmitted to a manufacturer of AR glasses. Also, a customer can be shown which possibilities there are for displaying AR information based on his or her center of rotation.

Figure 5:
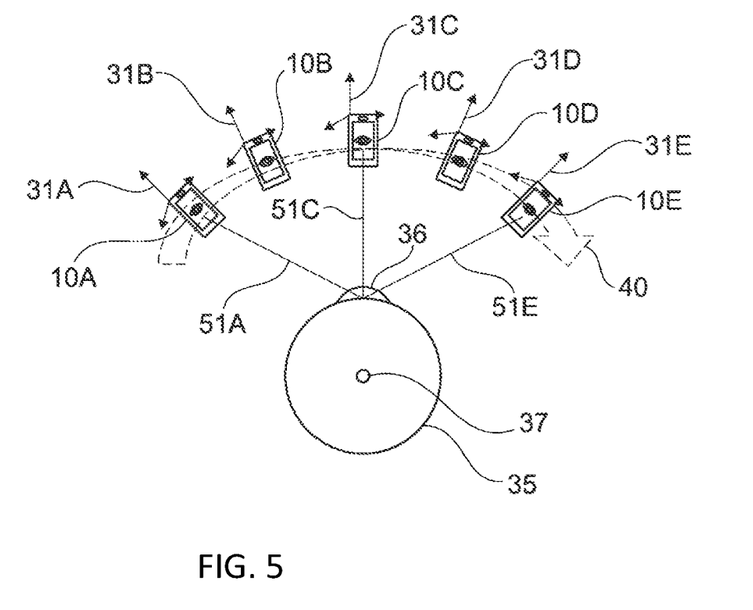
FIG. 5 shows the determination of the pupil size of an eye.

FIG. 5 illustrates steps 21 to 24 of FIG. 2 for determining the position of the pupil. Elements corresponding to those of FIG. 4 bear the same reference numerals and will not be described again in detail. Also here, the five positions corresponding to mobile devices 10A to 10E are used as an example. It should be noted that the positions for determining the position of the pupil may be the same or different positions of mobile device 10 than for determining the position of the center of rotation, and also the number of positions may be different. In contrast to FIG. 4, during the determination of pupil position, the person keeps the head in the same position and continues to look straight ahead, such that pupil 36 remains in the same position for all images. To be able to correlate the pupil position determined in FIG. 5 with the position of the center of rotation determined in FIG. 4, the head needs to stay in the same position for the two measurements. This may also be tracked/controlled during the measurement by determining additional face landmarks in the images taken. With said three landmarks, the position of the head in the world coordinate system may be determined, which may be used to correct the measurements or to control whether the head is held still in the same position as required.

As the person looks straight ahead and the position of the pupil remains unchanged, lines from the mobile device (typically pupil, more typically pupil center in the image) determined as in FIG. 4, of which lines 51A, 51C, and 51E are shown for three positions, intersect at pupil 36. In this way, the pupil position is determined.

For further use, the pupil position may then be given relative to the pupil center and may be transmitted to a manufacturer of AR glasses together with the center of rotation of the eye. Also, a customer can be shown which possibilities there are for displaying AR information based on his or her center of rotation. In other exemplary embodiments, with similar approaches as shown in FIGS. 4 and 5, other parts of the face, like nose tip, may be determined, and the position of the center of rotation may be given in relation to such other landmarks.

Returning now to FIG. 2, based on the position of the pupil and the position of the center of rotation, the eye diameter may be estimated. A simple estimation according to $d=2|p-c|_2$, where $\|\cdot\|_2$ is the $L_2$ vector norm giving the Euclidian distance between the pupil position p and the position of the center of rotation c. d is then the diameter. In other exemplary embodiments, to refine the estimation, corrections may be applied as discussed above.

By monitoring the diameter over time, myopia may be diagnosed as discussed above. For this, mobile device 10 may store measurements over time and issue an alert in case significant changes occur.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer-implemented method for determining a position of a center of rotation of an eye of a person in an arbitrary world coordinate system using a mobile device including a camera, at least one sensor, and at least one of a display or a loudspeaker, the method comprising:
   capturing a first image while the person looks in a first direction;
   capturing a second image while the person looks in a second direction; and
   determining the position of the center of rotation based on the first image and the second image,
   wherein capturing the first image includes capturing the first image with the camera of the mobile device while the mobile device is in a first position relative to a head of the person in the arbitrary world coordinate system, wherein the first direction is a direction to the camera of the mobile device or a target displayed on the display of the mobile device in the first position,
   wherein the method further includes:
   displaying instructions on the display of the mobile device or outputting instructions from the loudspeaker of the mobile device to move, by the person or another person, the mobile device from the first position to a second position relative to the head of the person, wherein the first position and the second position in the arbitrary world coordinate system are determined using the at least one sensor of the mobile device,
   wherein capturing the second image includes capturing the second image with the camera of the mobile device while the mobile device is in the second position in the arbitrary world coordinate system different from the first position, wherein the second direction is a direction to the camera of the mobile device or a target displayed on the display of the mobile device in the second position,
   wherein the first and second images are captured while the person keeps their head in a same position with the eye looking in the first and second directions, respectively, and
   wherein determining the position of the center of rotation is further based on the first position of the mobile device and the second position of the mobile device.

2. The method of claim 1, wherein the at least one sensor includes an acceleration sensor, and wherein determining the first position and the second position comprises at least one from the group consisting of:
   integrating an acceleration of the mobile device when moving the mobile device to the first position, and
   integrating the acceleration of the mobile device when moving the mobile device to the second position.

3. The method of claim 1, further comprising:
  determining a first orientation of the mobile device in the first position using an orientation sensor of the mobile device; and
  determining a second orientation of the mobile device in the second position using the orientation sensor,
  wherein determining the position of the center of rotation is further based on the first orientation and the second orientation.

4. The method of claim 1, wherein determining the position of the center of rotation comprises:
  determining a first line from the first position of the mobile device to a position of the pupil of the eye of the person in the arbitrary world coordinate system when the person looks in the first direction, determined based on the first image;
  determining a second line from the second position of the mobile device to a position of the pupil of the eye of the person in the arbitrary world coordinate system when the person looks in the second direction, determined based on the second image; and
  determining the position of the center of rotation based on the first line and the second line.

5. The method of claim 1, further comprising:
  capturing a further first image with the camera of the mobile device while the mobile device is in a further first position in the arbitrary world coordinate system, while the person looks straight ahead and the head of the person is in a same position as when the first image is captured;
  capturing a further second image with the camera of a mobile device while the mobile device is in a further second position in the arbitrary world coordinate system, while the person keeps looking straight ahead and the head of the person is in the same position as when the first image is captured; and
  determining a position of the pupil of the eye based on the further first position of the mobile device and the further second position of the mobile device.

6. The method of claim 5, further comprising:
  determining the further first position and the further second position using the at least one sensor of the mobile device.

7. The method of claim 6, wherein the at least one sensor includes an acceleration sensor, and wherein determining the further first position and the further second position comprises at least one from the group consisting of:
  integrating an acceleration of the mobile device when moving the mobile device to the further first position; and
  integrating the acceleration of the mobile device when moving the mobile device to the further second position.

8. The method of claim 5, further comprising:
  determining a further first orientation of the mobile device in the further first position using an orientation sensor of the mobile device; and
  determining a further second orientation of the mobile device in the further second position using the orientation sensor,
  wherein determining the position of the pupil is further based on the further first orientation and the further second orientation.

9. The method of claim 5, wherein determining the position of the pupil comprises:
  determining a further first line from the further first position of the mobile device to a position of the pupil of the eye of the person when the person looks straight ahead, determined based on the further first image;
  determining a further second line from the further second position of the mobile device to a position of the pupil of the eye of the person when the person looks straight ahead, determined based on the further second image; and
  determining the position of the pupil based on the further first line and the further second line.

10. A method for estimating a measure of an eye diameter based on the position of the pupil and the position of the center of rotation determined according to the method of claim 1.

11. The method of claim 10, wherein the method is performed repeatedly over time, and further comprises evaluating the measure of the eye diameter over time.

12. A method of manufacturing glasses or lenses, comprising:
  manufacturing the glasses or lenses based on the position of the center of rotation determined with the method of claim 1.

13. A mobile device for determining a center of rotation of an eye of a person in an arbitrary world coordinate system, the mobile device comprising:
  a camera;
  at least one sensor;
  at least one of a display or a loudspeaker; and
  a processor configured to control the mobile device to:
    capture a first image while the person looks in a first direction;
    capture a second image while the person looks in a second direction; and
    determine the position of the center of rotation based on the first image and the second image,
  wherein capturing the first image includes capturing the first image with the camera of the mobile device while the mobile device is in a first position relative to a head of the person in the arbitrary world coordinate system, wherein the first direction is a direction to the camera of the mobile device or a target displayed on the display of the mobile device in the first position,
  wherein the processor is further configured to cause the mobile device to display instructions on the display of the mobile device or to output instructions from the loudspeaker of the mobile device to move the mobile device from the first position to the second position relative to the head of the person, wherein the mobile device is configured to determine the first position and the second position in the arbitrary world coordinate system using the at least one sensor of the mobile device,
  wherein capturing the second image includes capturing the second image with the camera of the mobile device while the mobile device is in the second position in the arbitrary world coordinate system different from the first position, wherein the second direction is a direction to the camera of the mobile device or a target displayed on the display of the mobile device in the second position,
  wherein the mobile device is configured to output instructions such that the first and second images are captured while the person keeps their head in a same position with the eye looking in the first and second directions, respectively, and
  wherein determining the position of the center of rotation is further based on the first position of the mobile device and the second position of the mobile device.

14. The mobile device of claim 13, wherein the mobile device is configured to execute the method of claim 1.

15. A computer program for a mobile device stored on a non-transitory storage medium for determining a position of a center of rotation of an eye of a person in an arbitrary world coordinate system,
- wherein the mobile device includes a camera, at least one sensor, and at least one of a display or a loudspeaker,
- wherein the computer program, when executed by a processor of the mobile device, causes the mobile device to:
- capture a first image while the person looks at a first direction;
- capture a second image while the person looks at a second direction; and
- determine the position of the center of rotation based on the first image and the second image,
- wherein, capturing the first image includes capturing the first image with the camera of the mobile device while the mobile device is in a first position relative to a head of the person in the arbitrary world coordinate system, wherein the first direction is a direction to the camera of the mobile device or a target displayed on the display of the mobile device in the first position,
- wherein the computer program, when executed by the processor of the mobile device, further causes the mobile device to display instructions on the display of the mobile device or to output instructions from the loudspeaker of the mobile device to move the mobile device from the first position to the second position relative to the head of the person, wherein the mobile device is configured to determine the first position and the second position in the arbitrary world coordinate system using the at least one sensor of the mobile device,
- wherein capturing the second image includes capturing the second image with the camera of the mobile device while the mobile device is in the second position different from the first position, wherein the second direction is a direction to the camera of the mobile device or a target displayed on the display of the mobile device in the second position,
- wherein the computer program, when executed by the processor of the mobile device, further causes the mobile device to output instructions such that the first and second images are captured while the person keeps their head in a same position with the eye looking at the first and second directions, respectively, and
- wherein determining the position of the center of rotation is further based on the first position of the mobile device and the second position of the mobile device.

16. The computer program of claim 15, wherein the computer program, when executed by the processor, causes execution of the method of claim 1.

* * * * *